United States Patent
Liu et al.

(10) Patent No.: US 10,780,115 B2
(45) Date of Patent: Sep. 22, 2020

(54) PREPARATION OF ANTIMICROBIAL AGENT BASED ON ZNO/GQD-PEI COMPOSITES

(71) Applicant: Shaanxi University of Science & Technology, Xi'an, Shaanxi (CN)

(72) Inventors: Junli Liu, Shaanxi (CN); Jianzhen Shao, Shaanxi (CN); Jianzhong Ma, Shaanxi (CN); Hui Liu, Shaanxi (CN); Junqi Li, Shaanxi (CN)

(73) Assignee: Shaanxi University of Science & Technology, Xi'an (CN)

( * ) Notice: Subject to any disclaimer, the term of this patent is extended or adjusted under 35 U.S.C. 154(b) by 0 days.

(21) Appl. No.: 16/439,408

(22) Filed: Jun. 12, 2019

(65) Prior Publication Data

US 2020/0046764 A1 Feb. 13, 2020

(30) Foreign Application Priority Data

Aug. 9, 2018 (CN) .......................... 2018 1 0900202

(51) Int. Cl.
| | | |
|---|---|---|
| *A61K 33/30* | (2006.01) | |
| *A61K 47/59* | (2017.01) | |
| *A61K 33/44* | (2006.01) | |
| *B82Y 5/00* | (2011.01) | |
| *B82Y 30/00* | (2011.01) | |
| *B82Y 15/00* | (2011.01) | |

(52) U.S. Cl.
CPC .............. *A61K 33/30* (2013.01); *A61K 33/44* (2013.01); *A61K 47/59* (2017.08); *B82Y 5/00* (2013.01); *B82Y 30/00* (2013.01)

(58) Field of Classification Search
CPC ........ A63K 33/30; A63K 47/59; A63K 33/44; B82Y 5/00; B82Y 30/00; B82Y 15/00; C01B 2204/20; C01B 2204/00
See application file for complete search history.

(56) References Cited

FOREIGN PATENT DOCUMENTS

| | | |
|---|---|---|
| CN | 1310589 C | 4/2007 |
| CN | 103283781 B | 7/2014 |
| CN | 106376557 A | 2/2017 |
| CN | 104855419 B | 7/2017 |
| CN | 107372600 A | 11/2017 |

OTHER PUBLICATIONS

Liu et al. Antimicrobial Activity of Zinc Oxide-Graphene Quantum Dot Nanocomposites: Enhanced Adsorption on Bacterial Cells by Cationic Capping Polymers. ACS Sustainable Chem. Eng. 2019, 7:16264-16273. (Year: 2019).*

* cited by examiner

*Primary Examiner* — Robert A Wax
*Assistant Examiner* — Olga V. Tcherkasskaya
(74) *Attorney, Agent, or Firm* — Wayne & Ken, LLC; Tony Hom

(57) ABSTRACT

Preparation of high-performance antimicrobial agent based on ZnO/GODs-PEI composites. Nano ZnO is regarded as the effective antibacterial agents because of its distinctive photocatalytic properties. However, the fast recombination of photo-generated electrons and holes on the surface of ZnO seriously affects antibacterial activities. Therefore, numerous methods such as controlling the size and morphology of ZnO, doping metal and nonmetal ions, coupling semiconductor, constructing heterojunction and surface modification have been used to increase the activity of ZnO. The application aims to synthesize a stable low-dimensional ZnO/GQD aqueous with excellent dispersity and enhanced absorption to further improve its antibacterial activities. Hence, amphiphilic polyethylenimine-functionalized graphene quantum dots (GQD-PEI) was prepared firstly, which was then used to transfer ZnO NPs to water to obtain water-soluble ZnO/GODs-PEI composites.

3 Claims, 3 Drawing Sheets

US 10,780,115 B2

PREPARATION OF ANTIMICROBIAL AGENT BASED ON ZNO/GQD-PEI COMPOSITES

CROSS-REFERENCE TO RELATED APPLICATIONS

This application claims the benefit of priority from Chinese Patent Application No. 201810900202.X, filed on Aug. 9, 2018. The content of the aforementioned application, including any intervening amendments thereto, is incorporated herein with reference in its entirety.

TECHNICAL FIELD

The application relates to a novel high-efficiency antimicrobial agent, and more particularly to the preparation of a highly-active antimicrobial agent based on zinc oxide/graphene quantum dots-polyethyleneimine (ZnO/GODs-PEI) composites.

BACKGROUND

Recent years, improper exploitation of resources has caused scarcity of resources and damage to the natural environment, especially the increasing occurrence of "superbugs" is the serious health problem that has aroused worldwide concern. With the emergence and rapid progress of nanotechnology, the novel inorganic antibacterial agent-nanomaterials have received considerable attentions. Compared to traditional antibacterial materials, nanomaterials not only have the advantages such as durability, chemical stability, no pollution and low cost, but also possess unique physical and chemical characteristics to overcome the bacterial drug resistance. Therefore, inorganic nanomaterials are considered as the desired modus for environmental pollution remediation including the removal of bacteria and pathogens.

Nano ZnO is regarded as the effective antibacterial agent because of their distinctive photocatalytic properties. However, the aggregation of nanomaterial seriously affects its contact and absorption for bacteria, thus significantly weakening its antibacterial ability. Besides, the relatively poor biocompatibility and low absorption of ZnO also further hampered its antibacterial activities.

Since GQD-PEI has high electrical conductivity and good biocompatibility, combination of GQD-PEI could effectively improve the biocompatibility and water solubility, as well as inhibit the recombination of the photogenerated electrons and holes on the surface of ZnO. Herein, the present application aims to synthesize a stable low-dimensional ZnO/graphene quantum dots aqueous with excellent dispersity and enhanced absorption to further improve its antibacterial activities.

SUMMARY

An object of the invention is to provide a method of preparing a highly-active antimicrobial agent based on ZnO/GQDs-PEI composites to treat various bacterial infections.

The present invention discloses a method of preparing an antimicrobial agent based on ZnO/GQDs-PEI composites, comprising:

Step (1)

adding 1-10 g of citric acid to a 50 ml beaker and liquifying the citric acid by heating to 200° C. for 30 min to obtain an orange liquid; adding an aqueous sodium hydroxide solution to the orange liquid in a dropwise fashion to neutralize pH to 7.0; dialyzing the reaction mixture in Nanopure water for one day to obtain a GQD suspension;

Step (2)

diluting the GQD suspension obtained in step (1) to 0.2-2 mg/mL with deionized water; dispersing polyethyleneimine (PEI) into the diluted GQD suspension under ultrasonic processing for 10 min to obtain a homogeneous dispersion with a concentration of 5-15 mg/mL; adding 0.05-0.2 g of 1-ethyl-3-(3-dimethylaminopropyl) carbodiimide hydrochloride (EDC•HCl) to the reaction mixture; treating the reaction mixture by sonication for 20 min; adding additional EDC•HCl (0.2-0.5 g) to the reaction mixture under ultrasonic treatment for another 20 min and continuously stirring the reaction mixture for 24 h to produce GQD-PEI; and Step (3)

dispersing 0.2-1 g of an alkali source in 50 mL of ethanol by magnetic stirring for 30 min to produce solution A; dispersing 0.5-2 g of a zinc source in 100 mL of ethanol by magnetic stirring for 30 min to produce solution B; slowly dispersing the GQD-PEI obtained in step (2) in the solution B under sonication and dropwise adding the solution A to the reaction mixture under continuous stirring to start the reaction; heating the reaction mixture at 80-100° C. for 3-7 h; at last, washing the reaction mixture with ethanol and deionized water and dispersing the resulting product in an aqueous phase again to produce ZnO/GQDs-PEI composites.

In the present invention, PEI is used as a surface modification agent and the novel optoelectronic functional material ZnO is the main antibacterial ingredient. GQD-PEI with good biocompatibility and water solubility is formed by the combination of the amino group in the structure of PEI and the carboxyl group in GQD, and then GQD-PEI is combined with ZnO quantum dot to prepare the ZnO/GQD-PEI composite antibacterial agent. Therefore, the novel high-performance antimicrobial agent with good biocompatibility is designed and thus prepared. Compared to traditional antibacterial materials, the antimicrobial agent based on ZnO/GQD-PEI composites in the present invention has the advantages of good safety, environmental friendlessness as well as superior antimicrobial activity; for example, the minimum inhibitory concentration (MIC) of ZnO/GQDs-PEI composites against *E. coli* could reach 1.8 mg/mL.

DETAILED DESCRIPTION OF EMBODIMENTS

Figure 1:
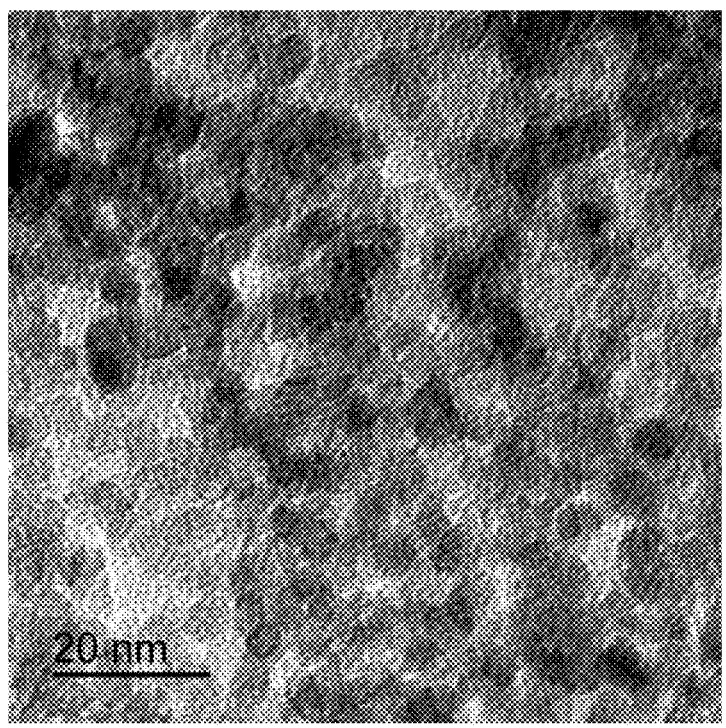
FIG. 1 is a TEM (transmission electron microscopy) image of ZnO/GQD-PEI composites prepared in the present invention.
Figure 2A:
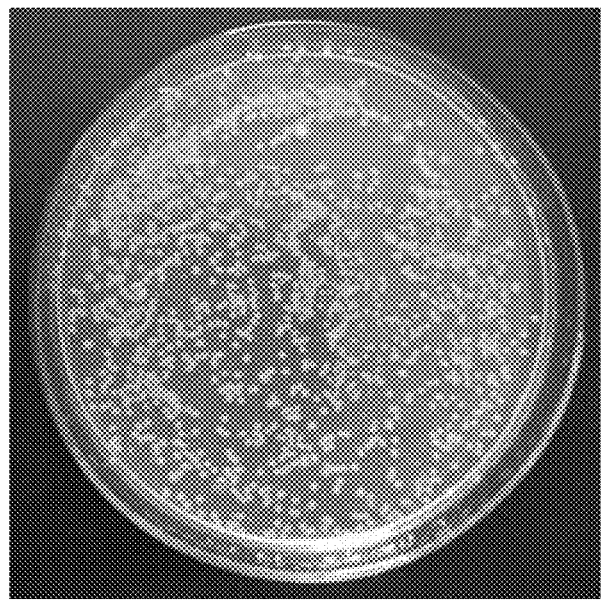
FIGS. 2a-b show the antimicrobial effect of the ZnO/GQD-PEI composites against *E. coli*. (a): blank (i.e., *E. coli* without treatment of ZnO/GQD-PEI composites); and (b) *E. coli* treated by ZnO/GQD-PEI composites.
Figure 2B:
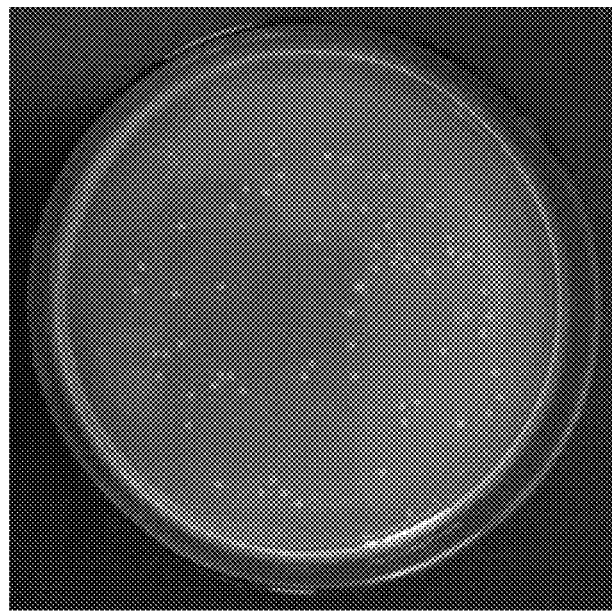
Figure 3:
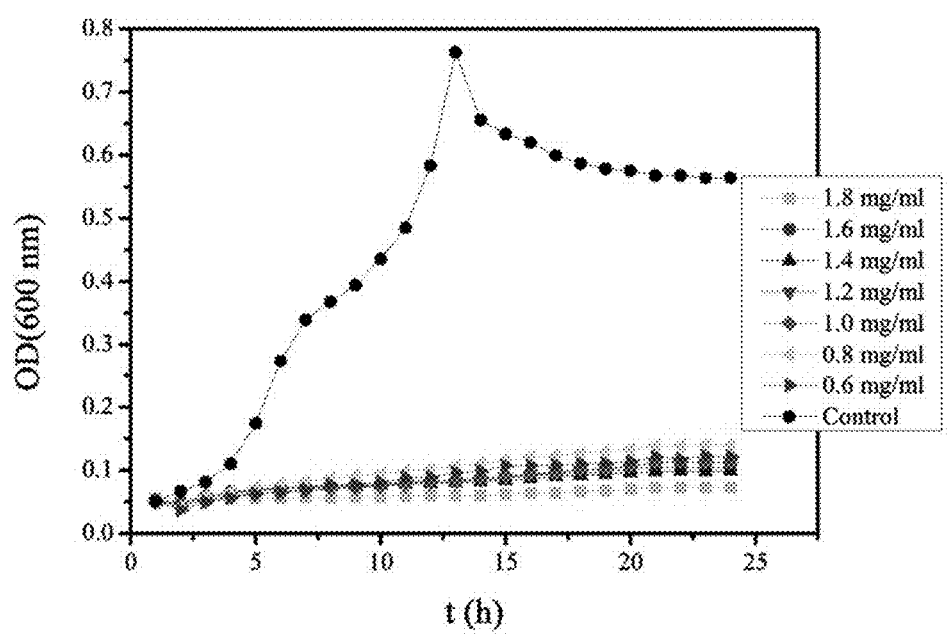
FIG. 3 shows growth curves of *E. coli* in nutritional broth containing ZnO/GQD-PEI composites for 24 h under ambient light.

The invention will be described in detail below with reference to the embodiments.

Example 1

Step (1)

Citric acid (CA, 2 g) was added to a 50 mL beaker and heated to 200° C. for 30 min to obtain an orange liquid. The reaction mixture was adjusted to pH 7.0 with dropwise addition of aqueous sodium hydroxide solution. Then, the obtained solution was dialyzed in Nanopure water for one day and collected.

Step (2)

GQD solution obtained in step (1) was diluted to 0.5 mg/mL with deionized water. Then polyethyleneimine (PEI) was dispersed into the diluted GQD suspension under ultrasonic processing for 10 min to obtain a homogeneous dispersion with the concentration of 8 mg/mL. 1-ethyl-3-(3-dimethylaminopropyl) carbodiimide hydrochloride (EDC•HCl, 0.1 g) was added to the above solution, and treated by sonication for 20 min. Next, additional EDC•HCl (0.3 g) was added under ultrasonic treatment for another 20 min, and stirred continuously for 24 h to produce GQD-PEI.

Step (3)

Briefly, potassium hydroxide (0.3 g) and zinc acetate dehydrate (0.587 g) were dispersed in 50 mL and 100 mL ethanol by magnetic stirring for 30 min to produce solution A and B, respectively. Then, the above obtained GQD-PEI in step (2) was slowly dispersed in the solution B under sonication for 10 min. The solution A was dropwise added to the reaction mixture under continuous stirring to start the reaction. The resulting mixture solution was heated at 95° C. for 5 h. At last, the product was washed with deionized water and ethanol, and dispersed in aqueous phase again. The products were denoted as ZnO/GQDs-PEI composites.

Example 2

Step (1)

Citric acid (CA, 4 g) was added to a 50 mL beaker and heated to 200° C. for 30 min to obtain an orange liquid. The reaction mixture was adjusted to pH 7.0 with dropwise addition of aqueous sodium hydroxide solution. Then, the obtained solution was dialyzed in Nanopure water for one day and collected.

Step (2)

GQD solution obtained in step (1) was diluted to 1.0 mg/mL with deionized water. Then polyethyleneimine (PEI) was dispersed into the diluted GQD suspension under ultrasonic processing for 10 min to obtain a homogeneous dispersion with the concentration of 10 mg/mL. 1-ethyl-3-(3-dimethylaminopropyl) carbodiimide hydrochloride (EDC•HCl, 0.12 g) was added to the above solution, and treated by sonication for 20 min. Next, additional EDC•HCl (0.388 g) was added under ultrasonic treatment for another 20 min, and stirred continuously for 24 h to produce GQD-PEI.

Step (3)

Briefly, potassium hydroxide (0.42 g) and zinc acetate dehydrate (0.78 g) were dispersed in 50 mL and 100 mL ethanol by magnetic stirring for 30 min to produce solution A and B respectively. Then, the above obtained GQD-PEI in step (2) was slowly dispersed in solution B under sonication for 10 min. The solution A was dropwise added to the reaction mixture under continuous stirring to start the reaction. The resulting mixture solution was heated at 95° C. for 5 h. At last, the product was washed with deionized water and ethanol, and dispersed in aqueous phase again. The products were denoted as ZnO/GQDs-PEI composites.

Example 3

Step (1)

Citric acid (CA, 6 g) was added to a 50 mL beaker and heated to 200° C. for 30 min to obtain an orange liquid. The reaction mixture was adjusted to pH 7.0 with dropwise addition of aqueous sodium hydroxide solution. Then, the obtained solution was dialyzed in Nanopure water for one day and collected.

Step (2)

GQD solution obtained in step (1) was diluted to 1.5 mg/mL with deionized water. Then polyethyleneimine (PEI) was dispersed into the diluted GQD suspension under ultrasonic processing for 10 min to obtain a homogeneous dispersion with the concentration of 12 mg/mL. 1-ethyl-3-(3-dimethylaminopropyl) carbodiimide hydrochloride (EDC•HCl, 0.15 g) was added to the above solution, and treated by sonication for 20 min. Next, additional EDC•HCl (0.37 g) was added under ultrasonic treatment for another 20 min, and stirred continuously for 24 h to produce GQD-PEI.

Step (3)

Briefly, potassium hydroxide (0.6 g) and zinc acetate dehydrate (0.796 g) were dispersed in 50 mL and 100 mL ethanol by magnetic stirring for 30 min to produce solution A and B, respectively. Then, the above obtained GQD-PEI in step (2) was slowly dispersed in solution B under sonication for 10 min. The solution A was dropwise added to the reaction mixture under continuous stirring to start the reaction. The resulting mixture solution was heated at 100° C. for 4 h. At last, the product was washed with deionized water and ethanol, and dispersed in aqueous again. The products were denoted as ZnO/GQDs-PEI composites.

Example 4

Step (1)

Citric acid (CA, 8 g) was added to a 50 mL beaker and heated to 200° C. for 30 min to obtain an orange liquid. The reaction mixture was adjusted to pH 7.0 with dropwise addition of aqueous sodium hydroxide solution. Then, the obtained solution was dialyzed in Nanopure water for one day and collected.

Step (2)

GQD solution obtained in step (1) was diluted to 2 mg/mL with deionized water. Then polyethyleneimine (PEI) was dispersed into the diluted GQD suspension under ultrasonic processing for 10 min to obtain a homogeneous dispersion with the concentration of 14 mg/mL. 1-ethyl-3-(3-dimethylaminopropyl) carbodiimide hydrochloride (EDC•HCl, 0.18 g) was added to the above solution, and treated by sonication for 20 min. Next, additional EDC•HCl (0.45 g) was added under ultrasonic treatment for another 20 min, and stirred continuously for 24 h to produce GQD-PEI.

Step (3)

Briefly, potassium hydroxide (0.8 g) and zinc acetate dehydrate (1.4 g) were dispersed in 50 mL and 100 mL ethanol by magnetic stirring for 30 min to produce solution A and B, respectively. Then, the above obtained GQD-PEI in step (2) was slowly dispersed in solution B under sonication for 10 min. The solution A was dropwise added to the reaction mixture under continuous stirring to start the reaction. The resulting mixture solution was heated at 100° C. for 4 h. At last, the reaction mixture was washed with deionized water and ethanol to produce ZnO/GQDs-PEI composites.

What is claimed is:

1. A method of preparing an antimicrobial agent based on ZnO/GQD-PEI composites, comprising:
    step (1)—adding 1-10 g of citric acid to a 50 ml beaker and liquefying the citric acid by heating to 200° C. for 30 min followed by adding an aqueous sodium hydroxide solution in a dropwise fashion to neutralize pH to 7.0; dialyzing said mixture for one day to obtain a GQD suspension;

step (2)—diluting the GQD suspension obtained in step (1) to 0.2-2 mg/mL with deionized water; dispersing polyethyleneimine (PEI) into the diluted GQD suspension under ultrasonic processing for 10 min to obtain a dispersion with a concentration of 5-15 mg/mL; followed by adding 0.05-0.2 g of 1-ethyl-3-(3-dimethylaminopropyl) carbodiimide hydrochloride (EDC•HCl); treating said mixture by sonication for 20 min; adding additional EDC•HCl (0.2-0.5 g) to said mixture under ultrasonic treatment for another 20 min and continuously stirring said mixture for 24 h to produce graphene quantum dot-polyethylenimine (GQD-PEI); and step (3)—dispersing 0.2-1 g of an alkali source in 50 mL of ethanol by magnetic stirring for 30 min to produce solution A; dispersing 0.5-2 g of a zinc source in 100 mL of ethanol by magnetic stirring for 30 min to produce solution B; dispersing the GQD-PEI obtained in step (2) in the solution B under sonication and dropwise adding the solution A under continuous stirring to make a reaction mixture; heating the reaction mixture at 80-100° C. for 3-7 h; washing the reaction mixture with ethanol and deionized water and dispersing the resulting product in an aqueous phase again to produce ZnO/GQDs PEI ZnO/GQD-PEI composites.

2. The method of claim 1, wherein in step (2), the PEI is present in an amount of 30-100 mg and used as a surface modification agent.

3. The method of claim 1, wherein in step (3), the alkali source is selected from the group consisting of potassium hydroxide, sodium hydroxide, lithium hydroxide, and combination thereof; and the zinc source is selected from the group consisting of zinc acetate dihydrate, zinc nitrate hexahydrate, and combination thereof.

* * * * *